United States Patent
Zhou (10) Patent No.: US 8,114,683 B2
(45) Date of Patent: Feb. 14, 2012

(54) LOW TEMPERATURE METHOD TO ENHANCE DETECTION OF MAGNETIC BEADS

(75) Inventor: Yuchen Zhou, Milpitas, CA (US)

(73) Assignee: Headway Technologies, Inc., Milpitas, CA (US)

( * ) Notice: Subject to any disclaimer, the term of this patent is extended or adjusted under 35 U.S.C. 154(b) by 1358 days.

(21) Appl. No.: 11/713,998

(22) Filed: Mar. 5, 2007

(65) Prior Publication Data

US 2008/0221432 A1 Sep. 11, 2008

(51) Int. Cl.
 *G01N 33/553* (2006.01)
(52) U.S. Cl. ...................................... 436/526
(58) Field of Classification Search .................. 436/526
See application file for complete search history.

(56) References Cited

U.S. PATENT DOCUMENTS

| | | | |
|---|---|---|---|
| 5,981,297 A | 11/1999 | Baselt | |
| 6,743,639 B1 | 6/2004 | Tondra et al. | |
| 6,875,621 B2 | 4/2005 | Tondra | |
| 7,048,890 B2 | 5/2006 | Coehoorn et al. | |
| 2006/0128035 A1 | 6/2006 | Coehoorn et al. | |
| 2007/0020701 A1 | 1/2007 | Menon et al. | |

OTHER PUBLICATIONS

"A biosensor based on magnetoresistance technology", by David R. Baselt et al., Biosensors and Bioelectronics 13 (7-8), 731-739 (1998) pp. 1-10.
"The BARC biosensor applied to the detection of biological warfare agents", by R.L. Edelstein et al., Biosensors & Bioelectronics, 14 (2000) 805-813.
"A DNA array sensor utilizing magnetic microbeads and magnetoelectronic detection", by M.M. Miller et al., Journal of Magnetism and Magnetic Materials, 225 (2001) 138-144.
"Single magnetic microsphere placment and detection on-chip using current line designs with integrated spin value sensors: Biotechnological application", by D.L. Graham et al., Jrnl of Appl. Phys. vol. 91, No. 10 May 15, 2002, pp. 7786-7788.
"Biodetection using magnetically labeled biomolecules and arrays of spin value sensors (invited)", by H.A. Ferreira et al., Jrnl. of Appl. Phys. vol. 93, No. 10, May 15, 2003, pp. 7281-7286.
"Detection of single micron-sized magnetic bead and magnetic nanoparticles using spin value sensors for biological applications", by Guanxiong Li et al., Jrnl. of Appl. Phys., vol. 93, No. 10, May 15, 2005, pp. 7557-7559.
"Model and Experiment of Detecting Multiple Magnetic Nanoparticles as Biomolecular Labels by Spin Valve Sensors", by Guanxiong Li et al., IEEE Trans. on Magnetics, vol. 40, No. 4, Jul. 2004, pp. 3000-3002.
"Towards a magnetic microarray for sensitive diagnostics", by Shan X. Wang et al., Jrnl. of Magnetism and Magnetic Materials, 293 (2005) 731-736.
"In situ detection of single micron-sized magnetic beads using magnetic tunnel junction sensors", by Weifeng Shen et al., Applied Phys. Letters 86, 253901-1 to 253901-3 (2005).
"Effect of spin-valve sensor magnetostatic fields on nanobead detection for biochip applications", by H.A. Ferreira et al., Jrnl. of Applied Phys. 97, 10Q904-1 to 10Q904-3 (2005).

(Continued)

*Primary Examiner* — Mark Shibuya
*Assistant Examiner* — Pensee Do
(74) *Attorney, Agent, or Firm* — Saile Ackerman LLC; Stephen B. Ackerman (57) ABSTRACT

Detection of magnetic beads at temperature below room temperature can increase the signal level significantly as compared to the same detection when performed at room temperature. Additional improvement is obtained if the beads are below 30 nm in size and if deviations of bead size from the median are small. A preferred format for the beads is a suspension of super-paramagnetic particles in a non-magnetic medium.

8 Claims, 5 Drawing Sheets

OTHER PUBLICATIONS

"Static and dynamic magnetic properties of spherical magnetite nanoparticles", by G.F. Goya et al., Jrnl. of Appl. Physics, vol. 94, No. 5, Sep. 1, 2003, pp. 3520-3528.

"Influence of the temperature dependence of anisotropy on the magnetic behavior of nanoparticles", by C. de Julian Fernández, Physical Review B 72, 054438-1 to 054438-10, (2005).

"Magnetic coercivity of $Fe_3O_4$ particle systems", by Sigurds Arajs et al., J. Appl. Phys. 69 (8), Apr. 15, 1991, pp. 5122-5123.

"Particle Size Analysis in Ferrofluids", by K. O'Grady et al., Jrnl. of Mag. and Mag. Materials 39 (1983) 91-94, North-Holland Publishing Co.

"A biosensor based on magnetoresistance technology", by David R. Baselt et al., Biosensors and Bioelectronics 13 (1998) 731-739.

*Physics of Ferromagnetism*, Second Edition, by Sōshin Chikazumi et al., Oxford Univ. Press, 1997, Preface and pp. 110-117.

"Ferromagnetic resonance in periodic particle arrays", by S. Jung et al., Physical Review B 66, 132401-1 to 132401-4, (2002).

"Ferromagnetic resonance of monodisperse co particles", by U. Wiedwald et al., J. Vac. Sci. Technol., A 19 (4), Jul./Aug. 2001, American Vacuum Society, pp. 1773-1776.

"Analytical and Micromagnetic Modeling for Detection of a Single Magnetic Microbead or Nanobead by Spin Valve Sensors", by Guanxiang Li et al., IEEE Trans. on Mag., vol. 39, No. 5, Sep. 2003, pp. 3313-3315.

08368007.4-2204 / 1967850 European Search Report, Mar. 24, 2010, Headway Technologies Inc.

"Magnetic field-assisted DNA hybridisation and simultaneous detection using micron-sized spin-valve sensors and magnetic nanoparticles," by D.L. Graham et al., Sensors and Actuators B 107(2005) 936-944, Elsevier.

"Magnetic labeling, detection, and system integration," by C.R. Tamanaha et al., Biosensors and Bioelectronics 24 (2008) 1-13, Elsevier.

FIG. 5C

LOW TEMPERATURE METHOD TO ENHANCE DETECTION OF MAGNETIC BEADS

FIELD OF THE INVENTION

The invention relates to the general field of magnetic beads attached to micro-structures with particular reference to the effect of temperature on signal strength.

BACKGROUND OF THE INVENTION

Detection of micro-structures such as biological or chemical molecules by using super-paramagnetic beads and particles as the labeling component and by using magneto-resistive sensors for detection of such labels is regarded as a promising technique to achieve accurate molecule counting with a resolution of several molecules or even a single molecule. It has the potential to enable fast, efficient, and economical biological applications, such as in-field virus and bacteria detection.

Binding assays to detect target molecules is a widely used technique in the biological, biochemical, and medical communities. The selective bindings commonly used include polynucleic acid bindings or hybridizations involving RNA and DNA, many types of ligand-to-receptor bindings, as well as antibody to antigen bindings. The target molecules in these bindings, for example, proteins or DNA, can also be a distinctive component or product of viruses, bacteria and cells, which may be the actual objects of interest for the detection.

In a binding assay, the binding molecules are attached to a solid substrate as "capture molecules". When the assay is exposed to a liquid-form sample, where the target molecules attached to a physical label are contained, the binding molecules capture the target molecules with the selective bindings and immobilize the target molecules on the surface. This capture process is called "recognition". The recognition events can be made to generate detectable signals from the attached labels and, consequently, the presence or absence of a target molecule can be detected.

In various prior art techniques utilizing the labeled binding process, the labels originally attached to the target molecule are also immobilized on the surface after the recognition process. The labels are either bound together with the target molecules on the surface ("sandwich" assay) or are by themselves ("competitive" assay). After the removal of non-bound labels, the bound labels can then be made to generate measurable signals.

When using magnetic beads or particles as the labeling component and an MR sensor as the signal generator, the MR devices are embedded underneath the binding surface and covered by a protective layer. When the magnetic beads or particles are bound to the surface on the top of a MR sensor, they can generate a magnetic field spontaneously, or, for super-paramagnetic beads or particles, in the presence of an applied magnetic field. This magnetic field from the beads or particles can be sensed by the MR sensor, which can then provide a voltage signal when driven by a sense current.

The magnetic labels reported in previous studies [1-10] or as patents [11-13] are usually super-paramagnetic beads or nano-particles that do not possess magnetization at room temperature without externally applied magnetic field because of the super-paramagnetic effect. Such labels in biological applications are desired because they do not agglomerate at zero field condition. The particles or beads used in this prior art work usually ranges from tens of nanometers to several microns. When the labels are attached to the surface after the recognition process, either multiple labels are attached on one MR device or there is one label per device. However, the sensing mechanism is generally the same for all the previous designs. When the magnetic labels are attached to the MR sensor top surface, the field generated by the magnetic moment of the beads or particles will either act directly on a MR sensor underneath it or will cancel out a portion of the applied magnet field acting on the sensor. For sensors having no labels attached, the magnetic field from the magnetic labels is not present.

Figure 1:
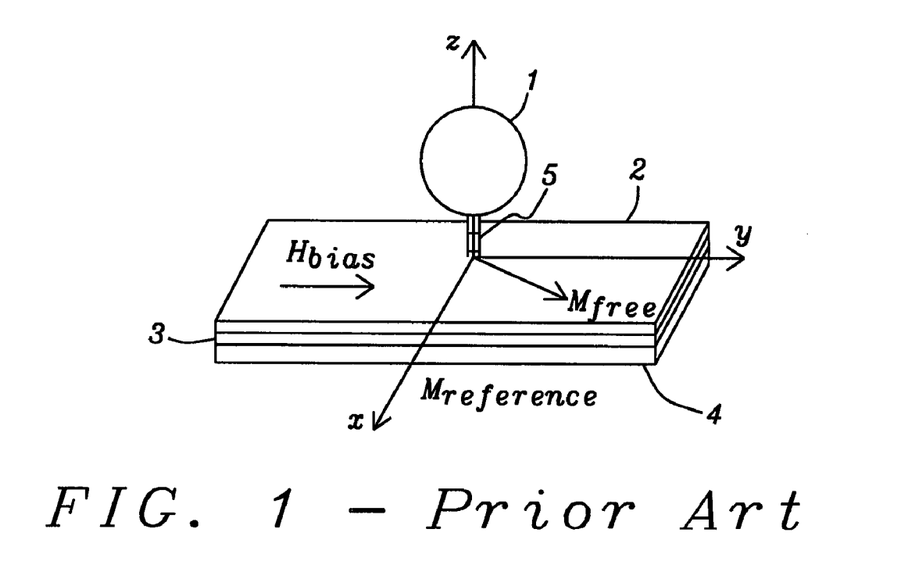
FIG. 1 illustrates the preferred method that is used to detect the presence of magnetic fields generated by the micro-beads.

FIG. 1 shows a schematic of the scheme described above. The magnetic bead 1 (by 'magnetic beads', we include, as well, particles and nano-particles) is attached to the MR sensor surface by the binding pairs 5 after the recognition process. The MR sensor used or referred to is usually a giant-magneto-resistive (GMR) or a tunneling-magneto-resistive (TMR) sensor, which contains a magnetic free layer 2, a non-magnetic spacer layer 3 and a magnetic reference layer 4. Spacer 3 is usually a conductive layer for GMR sensors and an insulator for TMR sensors. Magnetization of the reference layer 4, as represented by $M_{reference}$, is fixed in the X axis direction by an exchange field from other magnetic layers underneath, which are not shown in the figure.

Reference layer magnetization does not change direction under normal magnetic fields. In a conventional MR sensor, a bias DC field $H_{bias}$ is usually applied in the Y axis direction by two hard magnets on the sides of the sensor, so that the free layer's magnetization will be in the Y axis direction when no magnetic field is applied. However, this free layer alignment with the Y axis can also be achieved by making the sensor dimension along the Y axis longer than in X axis due to the shape anisotropy. Because of the shape anisotropy of thin film, the magnetization of the free layer 2, as represented by $M_{free}$, can only rotate freely in the XY plane when a transverse field is applied along the X axis direction and is very difficult to be made to rotate outside the XY plane towards the Z axis.

With a magnetic field applied in the X axis direction, the free layer magnetization rotates away from the Y axis and the resistance of the entire MR junction will change according to $R=R_0-\Delta R \cos(\theta)/2$, where $R_0$ is the base resistance of the sensor, $\Delta R$ is the full range resistance change of the sensor and $\theta$ is the angle between the magnetization of the reference layer and the free layer. With a DC current applied to the device, where the current can either flow in the XY plane or perpendicularly through the device, the voltage across the device will change because of the resistance change to produce a measurable voltage signal.

In prior studies and patents, several detection schemes were used. One commonly used scheme is applying a magnetic field in the transverse direction [4-10, 12-13], i.e. along the X axis in FIG. 1. Super-paramagnetic beads are also used. When a super-paramagnetic bead is bound to the top surface of the MR sensor, this applied field can magnetize the bead magnetization along the field direction. The bead magnetic moment in turn will produce a magnetic field in the MR sensor below and will partially cancel the originally applied magnetic field acting on the MR sensor. Therefore, the voltage across the sensor when a bead is present is different from when there is no bead attached, under the same applied field conditions, and the presence of the bead is detected by this voltage amplitude difference. A reference sensor to which beads will not attach at any time is normally used for comparison of this voltage difference. During the detection, the applied field can also be a modulated AC field that will induce the same frequency AC voltage across the sensor. By utilizing a lock-in technique, the signal to noise ratio can be enhanced.

Another bead sensing scheme, also known as BARC [1-3, 11], is applying a DC field perpendicular to the film plane, i.e. along the Z axis direction in FIG. 1. This DC field serves to magnetize the super-paramagnetic bead moment vertically. The in plane component of the field generated by the vertical bead moment will rotate the free layer magnetizations in the upper XY plane and low XY plane towards or away from the Y axis at the same time. If the reference layer magnetization is aligned along the Y axis, or a multi-layer MR structure is used, this rotation will produce a resistance change. It is also called "scissoring mode" [11]. This scheme also needs a reference sensor for the detection.

One problem associated with these previously published or patented bead-MR sensor detection methods is that the signal produced by the MR sensor from the magnetic moment of the magnetic labels is relatively small, i.e. less than 10% of the full MR range of the sensor in most cases. This small signal amplitude is especially problematic if high speed detection by a large number of sensors is required as in an applicable binding assay. Since higher speed needs wider detection bandwidth, which in turn introduces additional noise, with the noise power increasing with bandwidth, the low amplitude of the signal becomes a limiting factor. An FMR detection scheme that was recently disclosed in application Ser. No. 11/528,878, filed on Sep. 28, 2006, can help solve the problem in a different way. In general, then, higher detectable magnetic moments from magnetic labels are always beneficial from a signal-to-noise point of view in both conventional and future MR detection methods.

REFERENCES

[1] D. R. Baselt et al., "A biosensor based on magnetoresistance technology," *Biosens. Bioelectron.*, vol. 13, pp. 731-739, October 1998.
[2] R. L. Edelstein et al., "The BARC biosensor applied to the detection of biological warfare agents," *Biosens. Bioelectron.*, vol. 14, pp. 805-813, January 2000.
[3] M. M. Miller et al., "A DNA array sensor utilizing magnetic microbeads and magnetoelectronic detection," *J. Magn. Magn. Mater.*, vol. 225, pp. 138-144, April 2001.
[4] D. L. Graham, H. Ferreira, J. Bernardo, P. P. Freitas, and J. M. S. Cabral, "Single magnetic microsphere placement and detection on-chip using current line designs with integrated spin valve sensors: Biotechnological applications," *J. Appl. Phys.*, vol. 91, pp. 7786-7788, May 2002.
[5] H. Ferreira, D. L. Graham, P. P. Freitas, and J. M. S. Cabral, "Biodetection using magnetically labeled biomolecules and arrays," *J. Appl. Phys.*, vol. 93, pp. 7281, May 2003.
[6] G. Li et al., "Detection of single micron-sized magnetic bead and magnetic nanoparticles using spin valve sensors for biological applications," *J. Appl. Phys.*, vol. 93, pp. 7557-7559, May 2003.
[7] G. Li, S. X. Wang and S. Sun, "Model and experiment of detecting multiple magnetic nanoparticles as biomolecular labels by spin valve sesnors," *IEEE Trans. Magn.*, vol. 40, pp. 3000, 2004
[8] S. X. Wang et al., "Towards a magnetic microarray for sensitive diagnostics," *J. Magn. Magn. Mater.*, vol. 293, pp. 731-736, 2005.
[9] W. Shen, X. Liu, D. Mazumdar and G. Xiao, "In situ detection of single micron-sized magnetic beads using magnetic," *Appl. Phys. Lett.*, vol. 86, pp. 253901, 2005.
[10] H. Ferreira, N. Feliciano, D. L. Graham and P. P. Freitas, "Effect of spin-valve sensor magnetostatic fields on nano-bead detection," *J. Appl. Phys.*, vol. 97, pp. 10Q904, 2005.
[11] D. R. Baselt, "Biosensor using magnetically detected label," U.S. Pat. No. 5,981,297 (1999)
[12] M. C. Tondra, "Magnetizable Bead Detector," U.S. Pat. No. 6,743,639 B1 (2004)
[13] M. C. Tondra, "Magnetizable Bead Detector," U.S. Pat. No. 6,875,621 B2 (2005)
[14] G. F. Goya, T. S. Berquo, F. C. Fonseca and M. P. Morales, "Static and dynamic magnetic properties of spherical magnetite nanoparticles," *J. Appl. Phys.*, vol. 94, pp. 3520, 2003.
[15] C. de Julian Fernandez, "Influence of the temperature dependence of anisotropy on the magnetic behavior of nanoparticles," *Phys. Rev. B*, vol. 72, pp. 054438-1, 2005.
[16] S. Arajs, N. Amin and E. Anderson, "Magnetic coercivity of $Fe_3O_4$ particle systems," *J. Appl. Phys.*, vol. 69, pp. 5122, 1991.
[17] K. O'Grady and A. Bradbury, "Particle size analysis in ferrofluids," *J. Magn. Magn. Mater.*, vol. 39, pp. 91, 1983.
[18] S. Chikazumi, "Physics of Ferromagnetism,", $2^{nd}$ Edition, 1997, Oxford University Press, p.p. 113.

In addition to the above, the following references of interest were found as part of a routine search:

In U.S. Pat. No. 7,048,890 Coehoorn et al. teach detecting magnetic particles using differential measurements between two sensor elements while maintaining independence from outside influences such as temperature and, in U.S. 2006/0128035, Coehoorn et al. mention SQUID flux detectors that are expensive and operate at cryogenic temperatures (less than −73.3° C.).

SUMMARY OF THE INVENTION

It has been an object of at least one embodiment of the present invention to increase the detectable magnetic moment of magnetic beads (including magnetic particles and magnetic nano-particles) by measuring said moment with MR sensors at a temperature below that at which biological and chemical binding processes are normally performed.

Another object of at least one embodiment of the present invention has been for no agglomeration of magnetic beads to occur during biological and chemical procedures, while at the same time maximizing the signal during the low temperature detection by means of proper control of particle size distribution.

Still another object of at least one embodiment of the present invention has been to achieve the two previous objects by providing a method that requires minimum change the methods already in use.

These objects have been achieved by means of a methodology that enhances detection of said magnetic beads by a magneto-resistive (MR) sensor by reducing the environmental temperature during detection. These magnetic beads, particles or nano-particles can be used as magnetic labels in biological, chemical or other applications for detection of biological or chemical elements, such as molecules, viruses, bacteria, cells and chemical compounds. This method works by increasing the magnetic moment of the magnetic beads, particles or nano-particles that is induced by an applied magnetic field, which is the physical quantity that is detected by the MR sensors.

In general, the beads, or the magnetic particles of which the beads are comprised, should be super-paramagnetic thereby eliminating any magnetic attraction between them in the absence of an applied field. This greatly reduces the chances of bead agglomeration. It has also been found that the size of the basic magnetic particles should generally be less than about 30 nanometers with maximum deviations of particle size from the median being related to the median value (see FIG. 2) such that the greater the median the less the maximum deviation, and vice versa, with no universal limit to size deviation.

DESCRIPTION OF THE PREFERRED EMBODIMENTS

The invention relates to a method to enhance the detection by a magneto-resistive (MR) sensor of magnetic beads, magnetic particles and magnetic nano-particles, by reducing the environmental temperature during the detection. The magnetic beads, particles or nano-particles can be used as the magnetic labels in biological, chemical or other applications for detection of biological or chemical elements, such as molecules, viruses, bacteria, cells and chemical compounds. This method is aimed at increasing the magnetic moment of the magnetic beads, particles or nano-particles that is induced by an applied magnetic field, which is the detectable physical quantity for the MR sensors.

Super-Paramagnetic Relaxation

Super-paramagnetic labels are made either by suspension of magnetic nano-particles in non-magnetic matrix, for example as in Dynabeads (available from the Invitrogen company located at www.invitrogen.com), or directly with nano-particles as the labeling unit [8]. The magnetic nano-particles used in these labels are usually several nanometers up to tens of nanometers in diameter. At these sizes, the particles are super-paragmagnetic in zero magnetic field at room temperature. This effect is described by the Néel-Arrhenius law $$\tau = \tau_0 \exp\left(\frac{E}{k_B T}\right) \quad (1)$$

where $\tau$ is the relaxation time for the magnetization of the nano-particle to switch spontaneously because of thermal agitation. $\tau_0$ is the period of the thermal agitation events that is usually taken as between $10^{-9}$-$10^{-11}$ second. $k_B T$ is the Boltzmann constant times the temperature in Kelvin representing the thermal agitation energy. E is the nano-particle magnetic energy. For zero applied field, E is essentially the crystalline anisotropy energy of the nano-particle and is in the form of $E=K_{eff}V$, where V is the particle volume and $K_{eff}$ is the effective anisotropy of the particle that may be a function of the temperature, particle size, the particle material [14,15] as well as the packing density [16] of the particles. For an applied field that is much larger than the anisotropy field of the particle at the temperature, $E=M_s HV$, where H is the applied magnetic field and $M_s$ is the saturation magnetization of the particle material. For a physical measurement of the particle magnetization at a given temperature, if the measurement time is $\tau_m$, for the particle to be stable and maintain its magnetization during the measurement, i.e. not to relax, the volume of the particle needs to satisfy $$V \geq \frac{k_B T \ln(\tau_m/\tau_0)}{K'} \quad (2)$$

where $K'=K_{eff}$ when the magnetization is maintained by the anisotropy field of the particles itself or $K'=M_s H$ when it is maintained by the applied field. The temperature at which a magnetic nano-particle with a given particle volume V relaxes after a time of $\tau_m$ is usually referred to as the blocking temperature, $T_B$ of the particle at the specified condition. Therefore, for smaller size particles, under the same relaxation time and testing condition, the blocking temperature is lower. This can be described by a modification of Eq. (2)

$$T_B = \frac{K'V}{k_B \ln(\tau_m/\tau_0)} \quad (3)$$

Enhancement of Magnetic Moment Through Low Temperature Detection

The idea of using low temperature detection aims to satisfy the non-agglomeration requirement for the biological or chemical binding processes at room temperature, while at the same time achieving maximum magnetic signal output during the subsequent detection procedure.

A simple description of the ideal scenario is as follows: During the binding procedure, which is intrinsically a slow process, the particles are only experiencing low amplitude internal anisotropy field and weak interactions from surrounding particles. For particles to not agglomerate, size of the particles needs to satisfy $$V \leq \frac{k_B T_{rm} \ln(\tau_{bio}/\tau_0)}{K_{eff}} \quad (3)$$

where $T_{rm}$ is the temperature for the biological or chemical binding processes to occur, which is usually the room temperature, 300K. $K_{eff}$ is the self anisotropy of the particles that maintains its magnetization against relaxation caused by thermal agitation in the absence of any externally applied field. $\tau_{bio}$ is the relaxation time needed for the particle to be apparently 'non-magnetic' during the binding process. Since incubation time for biological binding applications usually takes hours of time, the relaxation time $\tau_{bio}$ in seconds is assumed to be short enough for an almost complete population of the particles to lose magnetic moment.

On the other hand, for detection of the nano-particles, the magnetization of the particles needs to be maintained without relaxation for a time period at least as long as the relaxation process. This maintained state is achieved through the application of an external field $H_a$ that introduces additional magnetic energy into the particle system to make relax slower. Particles that can maintain a magnetic moment under these conditions need to have their size satisfy $$V \geq \frac{k_B T_s \ln(\tau_s/\tau_0)}{M_s H_a} \quad (4)$$

The measurement time, $\tau_s$, can be estimated to be 0.01~1 second that corresponds to a bandwidth of 100 Hz~1 Hz. $T_s$ is the temperature at which the detection is performed. Therefore, particles that satisfy both Eq. (4) and Eq. (5) can be realized—no agglomeration during the binding process and presenting a full moment for detection. To get a rough estimation, parameters for $Fe_3O_4$ nano-particles are used as $M_s$=398 emu/cm$^3$, $K_{eff}$=$H_c M_s$/2=6.4×10$^4$ erg/cm$^3$ [14]. Room temperature at which the biological or chemical processes occur is $T_{rm}$=300K=27° C. The measurement temperature for the detection of the particle moment by MR sensor is set to T=250K≈−23° C. The applied field is $H_a$=600 Oe, which is arbitrarily chosen as a moderately high field that can be realized in applications where the magnetic labels are magnetized with a field perpendicular to the sensor plane [1-3,11]. Time constants used in the calculations are $\tau_0$=1e−10 sec, $\tau_{bio}$=1 sec and $\tau_s$=0.1 sec. From these listed parameters, particle diameter D needs to be:

17.9 nm≦D≦30.5 nm  (5)

which will satisfy the criteria of no agglomeration at room temperature and full saturation at the testing field and temperature. However, if testing temperature is further lowered to $T_s$=−80° C.=193K, the temperature at which biological samples are usually stored and preserved in laboratories as common practice, the particle size range can then be extended to 16.4 nm≦D≦30.5 nm. However, in the calculations, the saturation magnetization of the particles is assumed to be constant, but is theoretically higher at lower temperatures [14]. If this effect is taken into account, the lower boundary of the diameter range will be an even smaller number.

For comparison, if the measurement is done at room temperature with the same field application scheme, the particles that can contribute to the magnetic signal are within 19.0 nm≦D≦30.5 nm. Although the lower boundary seems to have no significant difference than the minimum of 16.4 nm as calculated previously, it will be shown in the next section that the magnetic signal from the lower boundary difference can be several times higher at low temperature than at room temperature depending on the size distribution of the particles.

Consideration of Particle Size Distribution

In real fabrication of magnetic nano-particles, particle sizes usually follow the log-normal distribution [17] as $$f(V) = \frac{1}{\sqrt{2\pi}\,\sigma V} \exp\left(-\frac{\ln^2(V/V_0)}{2\sigma^2}\right) \quad (6)$$

where $\sigma$ is the width of the distribution, V is the particle volume, $V_0$ is the median of the distribution related to the mean of the distribution $\bar{V}$ by $\bar{V}=V_0\exp(\sigma^2/2)$. For two different distributions, it is possible that the distribution with higher $V_0$ value will need a smaller $\sigma$ to maintain a given maximum allowable remnant magnetization in zero field at room temperature. If the median particle size of the distribution is gradually increased from zero, to satisfy the criteria of non-agglomeration, there exists a maximum $\sigma$ for each $V_0$, beyond which the non-agglomeration condition can no longer be satisfied.

In the following calculations we will consider three cases for which a population of particles that are super-paramagnetic in zero field at room temperature (D≦30.5 nm), contribute 99%, 99.9% or 99.99% of the total saturation moment of the entire particle system. Therefore, the particles with diameters from zero to 30.5 nm will account for 99%, 99.9%, or 99.99% of the total magnetization. In mathematical form, this is $\int_0^{D=30.5nm} Vf(V)dV = \eta \int_0^\infty Vf(V)dV$, where $\eta$=99%, 99.9% or 99.99%. Here, saturation magnetizations of the small and large particles are assumed to be the same.

The Langevin function as used in prior studies [14] is not implemented in this calculation. This is because the Langevin function for paramagnetic material mainly takes into account the spin orientation effect [18], where the magnetic spins are not aligned to the applied field direction. However, in superparamagnetic nano-particle systems, particle magnetization derives from the Zeeman energy from the applied field being higher than the thermal agitation. Therefore, the particle magnetizations should mainly align to the field direction so the Langevin function does not apply here.

Figure 2:
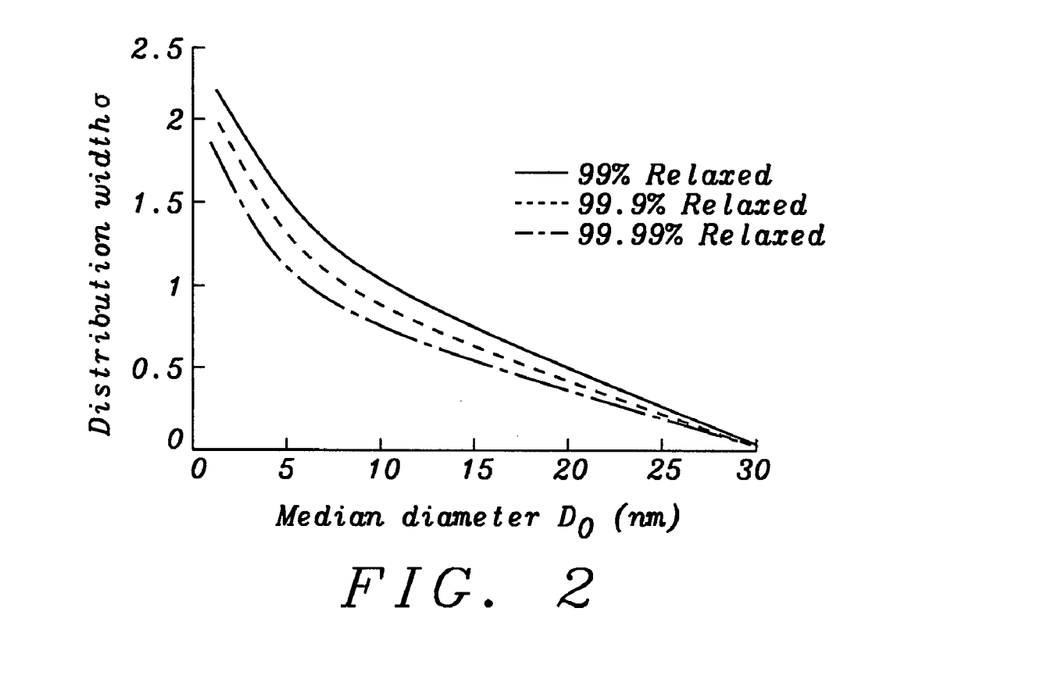
FIG. 2 plots the distribution of the maximum particle size deviation versus the median particle diameter at three different values of the percentage of particles that are superparamagnetic (99%, 99.9%, and 99.99%) at room temperature.

FIG. 2 shows a plot of the maximum distribution width vs. the median volume diameter determined by the above relaxation rates. It is clear that the higher the median value, the lower the maximum distribution that is allowed. The area beneath each of the curves represent the combination of median diameter and distribution width that will always satisfy the room temperature superparamagnetic conditions at the corresponding relaxation rate.

The difference between low temperature and room temperature measurements thus influences the difference between the lower diameter boundary for particles that do not relax during the measurement. From the previous section, the low diameter boundary for the room temperature measurement is 19 nm while for the low temperature (250K) measurement, it is 17.9 nm. The magnetic moments from the magnetic labels under the two testing conditions are respectively $$m_{rm}/m_s = \frac{\int_{D=19nm}^\infty Vf(V)dV}{\int_0^\infty Vf(V)dV} \quad (7)$$

$$m_{250K}/m_s = \frac{\int_{D=17.9nm}^{\infty} Vf(V)dV}{\int_{0}^{\infty} Vf(V)dV}$$

Figure 3A:
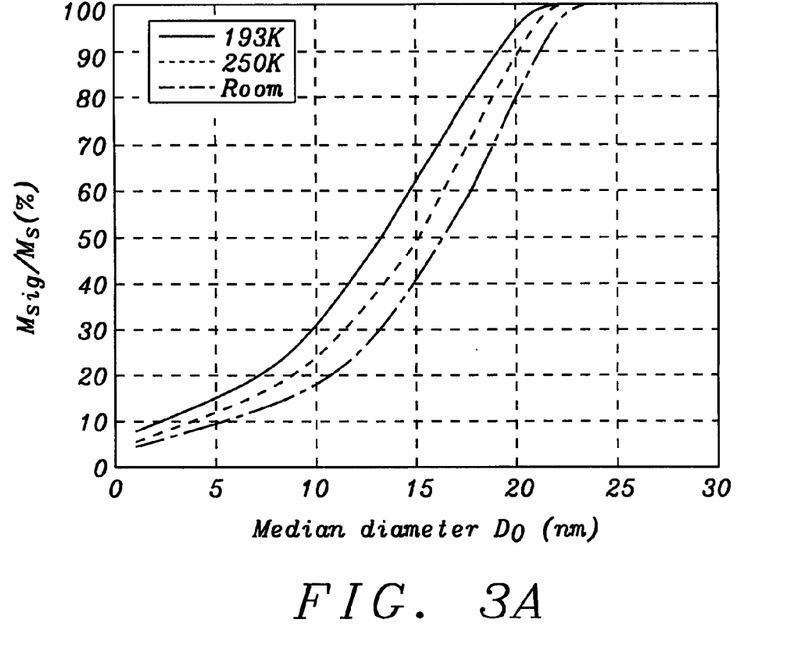
FIG. 3A plots (normalized) magnetic signal strength as a function of the median particle diameter for measurements at three different temperatures, 99% of the magnetic moment being superparamagnetic, at room temperature, and a 600 Oe external field for magnetizing the magnetic labels being assumed.

By following the 99% curve in FIG. 2, FIG. 3A shows the corresponding plot of the effective magnetization of the particle system vs. the particle median diameter for the three measurement temperatures—room temperature, 250K and 193K. The magnetization gained at the applied field of 600 Oe is shown as a percentage of the saturation magnetization. Clear differences can be seen between the three curves.

Figure 3B:
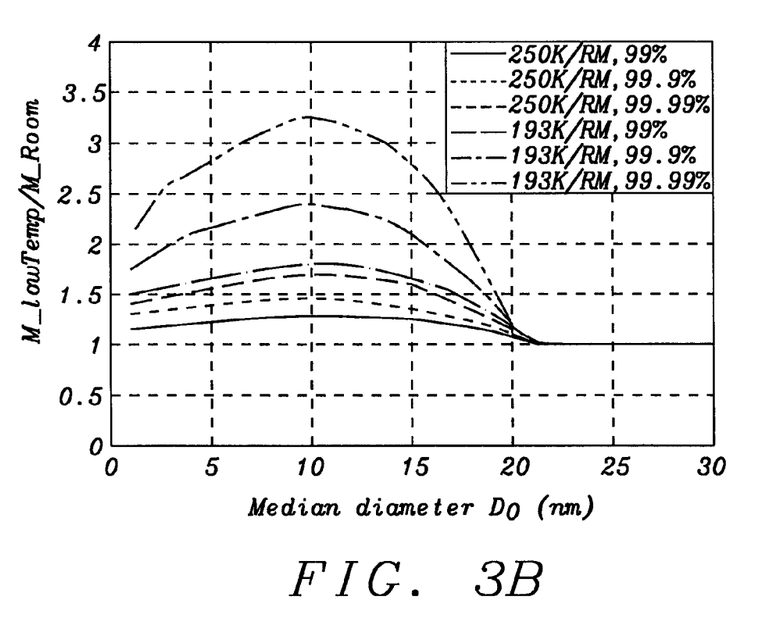
FIG. 3B plots the particle magnetic moment increase at low temperature at which the measurement was performed as a function of the median particle diameter for six different combinations of temperature and superparamagnetic percentage (which determines the particle size distribution for each median particle size value).

When, instead, the ratio of the gained magnetic moments is plotted, as plots of $M_{250K}/M_{rm}$ and $M_{193K}/M_{rm}$ vs. the median diameter, for the three curves seen in FIG. 2, FIG. 3B shows that the lower the measurement temperature the higher the gain in the magnetization obtained by using the low temperature measurement scheme. This gain is then reflected in the signal from the MR sensors during detection. A more than three times signal gain can be seen for the 193K 99.99% case. It also shows that the higher the relaxation ratio at room temperature, the greater the temperature gain. It is worth noting that, if the particle sizes are very uniform, the median value is around 30 nm, and the size distribution is very narrow (<0.1) at the same time, there is not much gain from the low temperature measurement as compared to the room temperature signal for the high applied field of 600 Oe case.

Figure 4A:
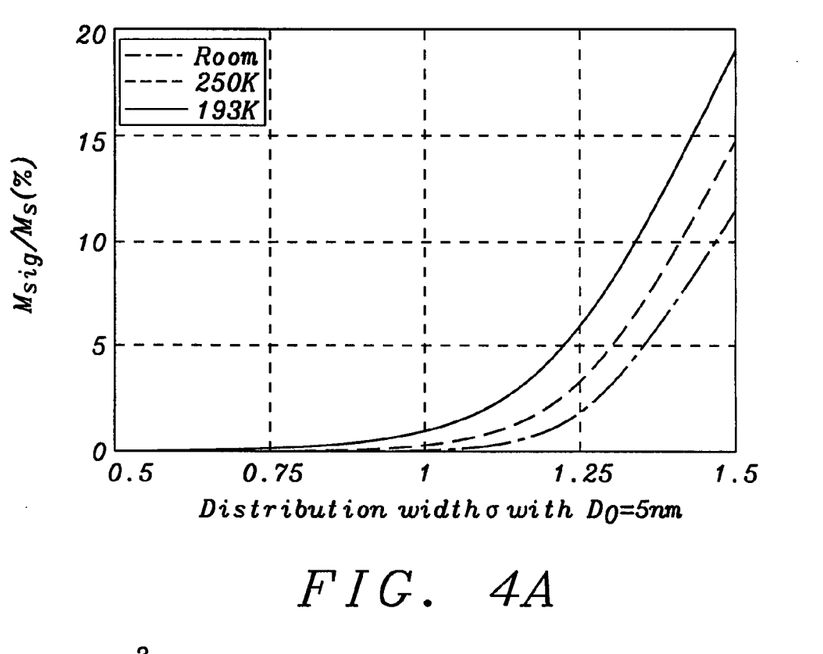
FIG. 4A plots (normalized) magnetic signal strength as a function of the particle size distribution for a particle size median of 5 nm diameter (and 600 Oe field).
Figure 4B:
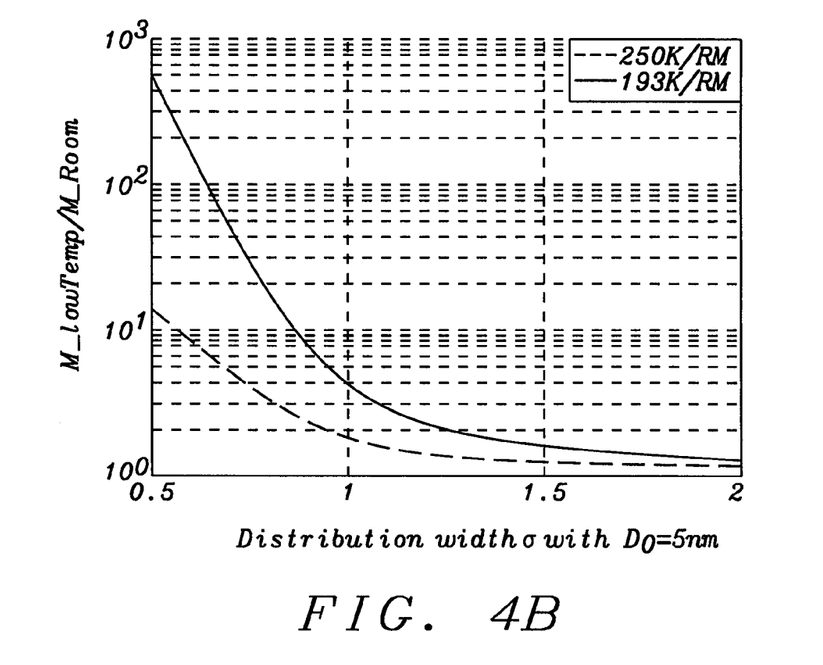
FIG. 4B plots the ratio of the magnetic signal strength at two different temperatures over the room temperature signal as a function of the particle size distribution.

FIG. 4 shows the case where the median diameter of the nano-particles is set at 5 nm and the distribution width varies from 0.5 to 1.5 [14-16]. FIG. 4A shows the magnetic moment vs. distribution width at room and low temperatures. FIG. 4B shows the gain of low temperatures over room temperature at different distribution widths. FIG. 4, shows that the temperature effect is more evident for the size distributions where the large size particles occupies a smaller fraction of the entire population. In other words, the fewer the number of large particles that are generating the room temperature signal, the more a lowering of the temperature will cause the signal to increase.

Figure 5A:
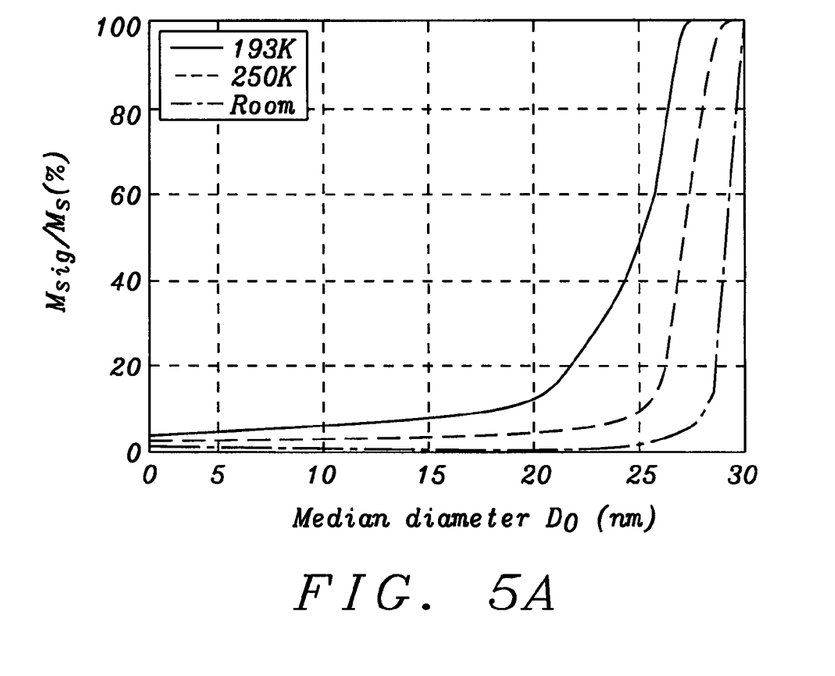
FIG. 5A plots the magnetic moment of a superparamagnetic particle vs, median particle size at three different temperatures. A 200 Oe applied field and a 99% super-paramagnetic particle ratio at room temperature and zero field are assumed.
Figure 5B:
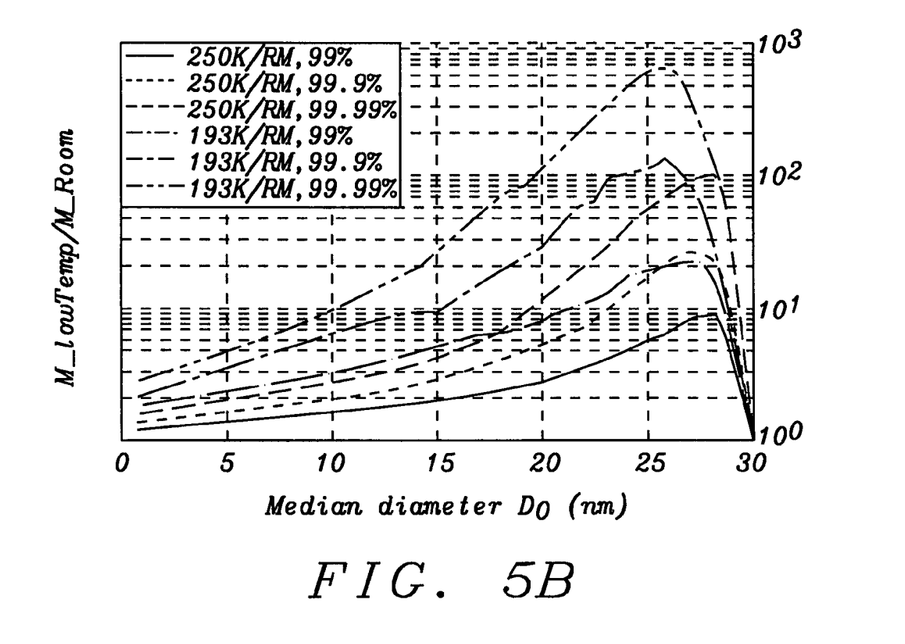
FIG. 5B shows the low temp./room temp. signal ratios vs. particle median diameter for three different super-paramagnetic ratios and two different low temperatures.

The above calculations have mainly focused on the case where a relatively large 600 Oe field is applied. However, there are applications where the field is applied transversely [4-10, 12-13] and the sensor saturates at high field. Maximum signal usually occurs in the 100-200 Oe applied field region [6-8]. To estimate the temperature effect at low field conditions, the applied field is now set at $H_a$=200 Oe. The particles that are non-magnetic at room temperature in zero field and that become magnetic in the applied field at room temperature, 250K, and 190K are respectively 29.5 nm≦D≦30.5 nm, 27.7 nm≦D≦30.5 nm and 25.3 nm≦D≦30.5 nm. Compared to the 600 Oe case, the lower boundary of the particles sizes has been increased by 10 nm. With these new boundaries, FIG. 5 shows similar plots as FIG. 3. FIG. 5A shows the magnetization vs. median diameter following the 99% curve in FIG. 2. FIG. 5B shows the ratio of magnetization obtained at 250K and 195K over the magnetization obtained at room temperature.

Figure 5C:
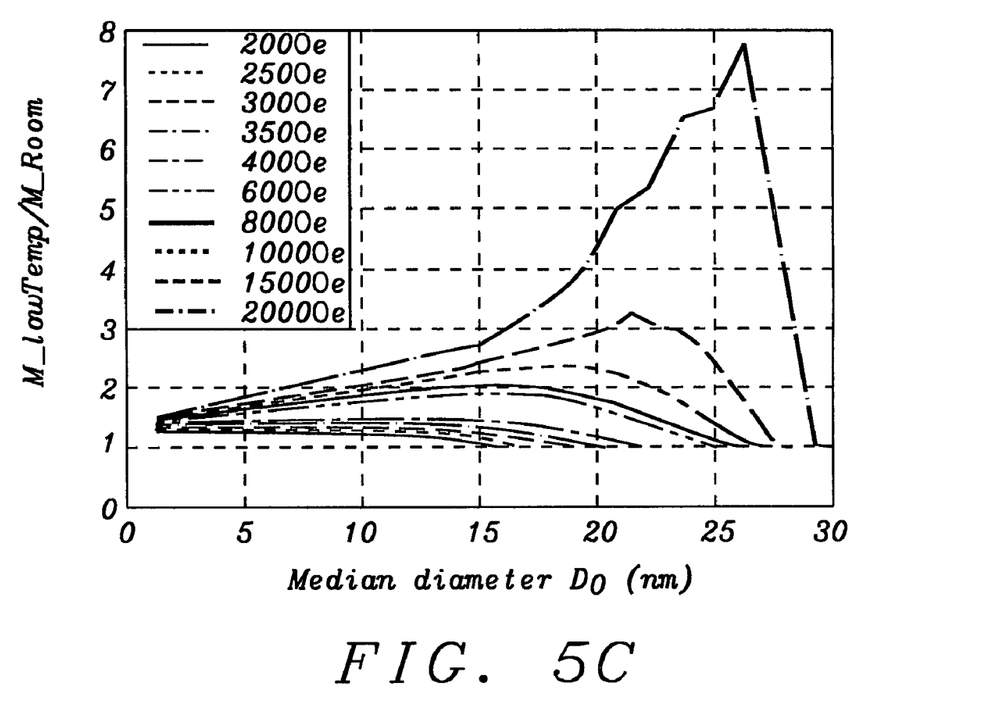
FIG. 5C shows how low temperature signal gain is affected by the applied field used to magnetize the superparamagnetic beads. The plot is similar to FIG. 5B with magnetic field strength as the parameter. A measurement temperature of 250K and a 99.9% superparamagnetic ratio are used.

The dramatic increase of the temperature effects in FIG. 5 as compared to FIG. 3 is mainly because the lower field magnetizes less of the small particles so most of the field comes from the large particles near the distribution tail. However, as the decreasing rate of the number of contributing large particles is different for the three temperatures as the measurement field decreases, the ratio of the absolute level of the signal at low temperature over room temperature is significantly enhanced at low fields. One other interesting point shown in FIG. 5 is that, at lower field, particle size distributions with high median value and small distribution width are more prone to show significant improvement (1-2 orders of magnitude higher) using the low temperature technique as compared to the 600 Oe applied field case seen in FIG. 2.

FIG. 5C shows a further exploration of the temperature effect on different applied field. In this plot, the applied field is now varied from 200 Oe to 2 kOe. For each of the fields, a lower particle diameter boundary is calculated for room and 250K temperatures. FIG. 5C shows the ratio of 250K over room temperature measurement vs. the median diameter for each of the applied fields. The median and distribution values used are for the 99.9% curve in FIG. 2. As shown in FIG. 5C, for a given distribution of the particle size, the lower the applied field, the greater the effect of the low temperature gain.

Low Temperature Detection Scheme Summary

In summary of the above calculations, the temperature improvement of the detection signal can be very significant. The actual performance improvement, however, depends on the nano-particle size distribution and magnetizing field amplitude being used.

For the detection methods that utilize a low amplitude magnetizing field, for example methods that use a transverse direction magnetizing field or require a stringent low remnant magnetization to avoid agglomeration, the improvement that results from low temperature detection can be very high. Additionally, increasingly lower temperature will produce increasingly greater improvements over room temperature detection.

For the same magnetizing field condition, the improvement is a function of the particle size distribution. This dependence also provides the possibility of achieving non-agglomeration at room temperature and maximum signal at lower temperature with enough particle size distribution control. Although it is likely that such control will also improve signal detection at room temperature, the degree of signal level increase is much higher for the low temperature detection scheme than at room temperature.

Advantages of the Low Temperature Measurement Scheme

The disclosed low temperature measurement method has advantages to assist existing and future MR detection schemes in the following ways:

1. The method has the potential of improving signal level by orders of magnitude over the same detection procedure performed at room temperature.
2. The method can fit into existing schemes that use an MR sensor to detect the presence of magnetic labels, without significant modification. The major difference is that the detection is performed in a lower temperature environment. The low temperature environment can be easily implemented with a simple cooling chamber by liquid nitrogen, dry ice, or similar cooling material, which may be provided in small packages for portable applications. Where applicable, ferroelectric cooling could also be used.
3. As nano-particle fabrication technology improves over time, particle sizes will become more uniform and size distribution will become smaller. For a smaller distribution of the particles, this low temperature method can help to increase the signal level significantly, particularly for a low amplitude applied field. In schemes where the particles are transversely magnetized, such low amplitude magnetizing fields and high magnetization gain are most desirable as these conditions enable the sensor's linear region to be better utilized.

4. Low temperatures not only enhance the magnetic signal, but also decrease the thermally related noise of the MT sensor, for example random magnetization fluctuation due to thermal agitation and Johnson noise. The noise power decrease is at least −0.8 dB if measurement is done at 250K and −1.8 dB if at 193K.

What is claimed is:

1. A method to improve detection of the presence of a magnetic bead, comprising:
   providing a plurality of micro-structures;
   at a first temperature, attaching a micro-bead to a binding site of a micro-structure;
   providing a detector that will signal the presence of a magnetic field; and
   at a second temperature, that is lower than said first temperature, through magnetization of said micro-bead, causing a detectable change in said detector's signal, thereby improving detection of the presence of said micro-bead and said micro-structure.

2. The method of claim 1 wherein said first temperature is room temperature and said second temperature is between about 30 and 222 K below room temperature.

3. The method of claim 1 wherein said micro-bead has magnetic properties selected from the group consisting of ferromagnetic, ferrimagnetic, paramagnetic and super-paramagnetic.

4. The method of claim 1 wherein, when said micro-bead exceeds about 0.1 microns in diameter and further comprises a suspension of smaller sized super-paramagnetic particles in a non-magnetic medium.

5. The method of claim 1 wherein said micro-bead has little or no spontaneous magnetic moment in zero magnetic field during physical, biological and chemical processes, and can gain a magnetic moment in the presence of a magnetic field.

6. The method of claim 1 wherein said detector and said micro-bead are cooled in a shared low temperature environment.

7. The method of claim 1 wherein improvements of low temperature detection, relative to room temperature detection, can be further enhanced by reducing size variations between super-paramagnetic particles to less than a log-normal distribution width of 2.

8. The method of claim 1 wherein improved low temperature detection, relative to room temperature detection, can be further enhanced through an improvement of said micro-bead's magnetic properties' selected from the group consisting of reduced crystalline anisotropy, increased sensitivity of magnetization to temperature, and reduced surface roughness of super-paramagnetic particles inside said micro-bead.

\* \* \* \* \*